US009005984B2

(12) United States Patent
Woloszczuk et al.

(10) Patent No.: US 9,005,984 B2
(45) Date of Patent: *Apr. 14, 2015

(54) DETERMINING FELINE PROBNP

(75) Inventors: Wolfgang Woloszczuk, Vienna (AT); Gerhard Hawa, Vienna (AT)

(73) Assignee: Biomedica Medizinprodukte GmbH & Co KG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 12/394,637

(22) Filed: Feb. 27, 2009

(65) Prior Publication Data

US 2009/0170136 A1    Jul. 2, 2009

Related U.S. Application Data

(63) Continuation of application No. 10/596,968, filed as application No. PCT/EP2005/054446 on Sep. 8, 2005.

(30) Foreign Application Priority Data

Sep. 8, 2004    (AT) ................ A 1505/2004

(51) Int. Cl.
| | | |
|---|---|---|
| *G01N 33/68* | (2006.01) | |
| *G01N 33/53* | (2006.01) | |
| *G01N 33/543* | (2006.01) | |
| *C07K 16/26* | (2006.01) | |

(52) U.S. Cl.
CPC .............. *C07K 16/26* (2013.01); *G01N 33/68* (2013.01); *G01N 2333/58* (2013.01); *G01N 2800/32* (2013.01); *C07K 2317/34* (2013.01)

(58) Field of Classification Search
None
See application file for complete search history.

(56) References Cited

U.S. PATENT DOCUMENTS

| | | | | |
|---|---|---|---|---|
| 5,114,923 | A | 5/1992 | Seilhamer et al. ........... 514/12 |
| 6,225,049 | B1 * | 5/2001 | Lan et al. ................... 435/6.13 |
| 6,586,396 | B1 | 7/2003 | Seilhamer et al. ........... 514/12 |
| 6,818,619 | B2 | 11/2004 | Burnett, Jr. et al. ......... 514/12 |
| 7,264,938 | B2 | 9/2007 | Borgya et al. ............... 435/7.1 |
| 7,264,939 | B2 | 9/2007 | Borgya et al. ............... 435/7.1 |
| 2004/0018577 | A1 | 1/2004 | Emerson Campbell et al. ....................... 435/7.93 |
| 2004/0096920 | A1 | 5/2004 | Davey et al. ................ 435/7.92 |
| 2004/0253637 | A1 * | 12/2004 | Buechler et al. ............ 435/7.1 |
| 2006/0051825 | A1 | 3/2006 | Buechler et al. ............ 435/7.93 |
| 2007/0059767 | A1 | 3/2007 | Karl et al. ................... 435/7.1 |
| 2009/0170135 | A1 * | 7/2009 | Woloszczuk et al. ........ 435/7.92 |

FOREIGN PATENT DOCUMENTS

| | | |
|---|---|---|
| EP | 0 648 228 | 11/1998 |
| EP | 0 016 867 | 1/2006 |
| WO | WO 00/35951 | 6/2000 |
| WO | WO 00/45179 | 8/2000 |
| WO | WO 00/71576 | 11/2000 |
| WO | WO 02/059567 | 8/2002 |
| WO | WO 03/087819 | 10/2003 |

OTHER PUBLICATIONS

Sisson et al. "Plasma Levels of ANP, BNP, Epinephrine, Norepinephrine, Serum Aldosterone, and Plasma Renin Activity in Healthy Cats and Cats Without Myocardial Disease" J. Vet. Intern Med 17 (2003), p. 438, Abstract No. 241.*
Harlow, E. and Lane, D., Antibodies: A Laboratory Manual (1988) Cold Spring Harbor Laboratory Press, Cold Spring Harbor, NY, pp. 72-77, 555-561, 578-582, and 591-592.*
The National Center for Biotechnology Information ("NCBI"), entry Q9GLK4 (ANFB_FELCA), version 10 dated Aug. 16, 2004, retrieved from http://www.uniprot.org/uniprot/Q9GLK4.txt?version=10 on Aug. 28, 2013, and accompanying revision history; four pages total.*
Asano et al., "Plasma atrial and brain natriuretic peptide levels in dogs with congestive heart failure," *J. Vet. Med. Sci.*, 61:523-9, 1999.
Biondo et al., "Immunohistochemistry of atrial and brain natriuretic peptides in control cats and cats with hypertrophic cardiomyopathy," *Vet. Pathol.*, 40:501-506, 2003.
Harlow and Lane, "Antibodies: a laboratory manual," Cold Springs Harbor Laboratory, Cold Spring Harbor, NY, pp. 23-24, 76, 319, 321-323, 342-345, 353, 561, 563, 574, 591-593, 1988.
Janeway et al., Immunobiology: the immune system in health and disease, Elsevier Science Ltd/Garland Publishing, New York, NY, 4th Ed., 34-35, 1999.
Jortani et al., "Strategies for developing biomarkers of heart failure," *Clin. Chem.*, 50:265-278, 2003.
Liu et al., "Cloning and characterization of feline brain natriuretic peptide," *Gene*, 292:183-190, 2002.
MacDonald et al., "Brain natriuretic peptide concentration in dogs with heart disease and congestive heart failure," *J. Vet. Intern. Med.*, 17:172-7, 2003.
Merrifield, "Solid Phase Peptide Synthesis. I. The Synthesis of a Tetrapeptide," *J. Am. Chem. Soc.*, 85:149, 1963.
Office Communication, issued in U.S. Appl. No. 10/596,968, dated Mar. 18, 2009.
Seidler et al., "The amnio terminal region of proANP oligomerise through leucine zipper-like coiled-coil motifs," *Biochemical and Biophysical Research Communications*, 255:495-501, 1999.
Swiss-Prot accession No. P16859, retrieved from the UniProtKP/Swiss-Prot database at http://www.uniprot.org/uniprot/P16859, on Mar. 10, 2009.
The Academic Press Dictionary of Science and Technology (definition for the term: "polyclonal," Oxford: Elsevier Science & Technology (1996), retrieved Oct. 22, 2008, from http://www.credoreference.com/entry/3144515.

(Continued)

*Primary Examiner* — Christine Foster
(74) *Attorney, Agent, or Firm* — Karim Lagobi (57) ABSTRACT

Methods and compositions are disclosed for determining feline proBNP or fragments thereof in a sample. In one method, feline proBNP or fragments thereof are determined by providing a feline sample, contacting the sample with at least one antibody that binds an epitope in the region from amino acids 68 to 80 of feline proBNP, and determining the presence of the feline proBNP or fragments thereof present in the sample. Antibodies that bind feline proBNP and kits comprising such antibodies are also disclosed.

4 Claims, 4 Drawing Sheets

(56) References Cited

OTHER PUBLICATIONS

Wolfe, Molecular and Cellular Biology, 790-793, 1993.
Goetze, "Biochemistry of Pro-B-Type Natriuretic Peptide-Derived Peptides: The Endocrine Heart Revisited," *Clin. Chem.*, 50:1503-1510, 2004.
Luchner et al., "Differential Expression of Cardiac ANP and BNP in a Rabbit Model of Progressive Left Ventricular Dysfunction," *Cardiovasc. Res.*, 51:601-607, 2001.
Thomas et al., "Haemodynamic Action of B-Type Natriuretic Peptide Substantially Outlasts its Plasma Half Life in Conscious Dogs," *Clin. Exp. Pharmacol. Physiol.*, 30:369-375, 2003.

\* cited by examiner

DETERMINING FELINE PROBNP

CROSS-REFERENCE TO RELATED APPLICATIONS

This application is a continuation of U.S. application Ser. No. 10/596,968 filed on 30 Jun. 2006, which is a U.S. national phase application under 35 U.S.C. §371 of International Application No. PCT/EP2005/054446 filed 8 Sep. 2005, which claims priority to Austrian Application No. A 1505/2004 filed 8 Sep. 2004. The entire text of each of the above-referenced disclosures is specifically incorporated by reference herein without disclaimer.

BACKGROUND

The present invention relates to a method of determining proBNP or fragments thereof in mammals.

Heart diseases play an important part not only in humans, but also animals, in particular pets, such as dogs or cats, are afflicted with these diseases. Studies have shown that, e.g., each tenth canine heart has a functional impairment. The heart diseases occurring concern, for instance, the cardiac valves and the cardiac muscle. Since at first the heart is capable of compensating functional impairment by working harder, such a disease in most cases remains hidden, with the consequence that the state of the heart will deteriorate due to the increased load on the heart. The symptoms resulting from heart diseases, such as fatigue, circulatory insufficiency, languor, can mostly be recognized when the pet's heart is no longer able to compensate the weakness. In such a case, the heart disease has already progressed so much that complete curing is hardly possible any more.

As a rule, chronic cardiac valve and cardiac muscle changes are not curable, yet by the use of medicaments, the further progress of the heart disease can be slowed down. Therefore, an early diagnosis must be made for the occurring heart diseases. By way of routine, mainly physical methods are used for this purpose, such as auscultation of the heart sounds, the recording of an electrocardiogram, X-ray and ultrasonic examinations. These examination methods mainly have the disadvantage that they can be carried out only when already visible or audible defects can be directly recognized on the heart. Furthermore, physical examination methods require suitable and, as a rule, expensive devices in order to carry out a respective diagnosis.

The heart diseases most frequently occurring in dogs, e.g., are heart decompensation and dilated cardiomyopathy, which mainly afflict big animals. Dilated cardiomyopathy is a heart disease which causes an enlargement of the ventricles of the heart with normal wall thickness, such enlargement quickly causing cardiac insufficiency in the afflicted animal. By admixing taurine to the feed, the risk of falling ill with dilated cardiomyopathy could be reduced significantly. In an illness related to dilated cardiomyopathy, the restrictive cardiomyopathy which frequently is found in older cats, a continuous decrease in the heart function with a reduced ability for pumping can be observed. The heart disease most frequently occurring in cats is hypertrophic cardiomyopathy. This disease of the cardiac muscle causes thickening of the heart wall and a resultant reduced ability to fill the ventricles of the heart with blood. This leads to an accumulation of blood in the left ventricle and to a greatly reduced amount of blood being pumped through the body.

In many heart diseases, such as, e.g., cardiac insufficiency, dilated cardiomyopathy, hypertrophic cardiomyopathy, left-ventricular hypertrophy and dysfunction, a peptide hormone, the so-called BNP (brain natriuretic peptide) is secreted. This hormone causes the excretion of liquid via the kidneys and thus regulates the cardiovascular system. Since this peptide is produced in the heart and is increasingly produced in case of an overstress and congestion of the heart, determining the BNP level in blood is a suitable means for evaluating cardiac insufficiency.

BNP as well as other natriuretic peptides play an important part in regulating the water balance and the blood pressure. If the cardiac wall is dilated, it secrets BNP in increasing amounts, causing an excretion of sodium and liquid via the kidneys and a dilation of the blood vessels, which in sum can lower the blood pressure and the filling level of the heart. BNP is synthesized by the cells of the cardiac muscle as proBNP which finally is cleaved into n-terminal proBNP and BNP. Both parts of the BNP are delivered to the blood and can be determined therein.

Cardiac diseases in animals are, inter alia, dealt with in the following pertinent publications: Bright J M and Cali J V, J Am Vet Med Assoc 2000, 216:1110-4; Guglielmini C, Vet Res Commun 2003, 27 Suppl 1:555; Boswood A et al., J Small Anim Pract 2003, 44:104-8; Takemura N et al., J Vet Med Sci 2003, 65:1265-7; MacDonald K A et al., J Vet Intern Med 2003, 17:172-7; Greco D S et al., Can Vet J 2003, 44:293-7; Monnet E et al., J Am Vet Med Assoc 1997, 211: 569-72; Hamlin R L et al., J Vet Intern Med 1996, 10:85-7; Gaschen L et al., J Vet Intern Med 1999, 13:346-56.

A large number of methods are already known in the prior art which assist in the detection of human proBNP or the fragments thereof, respectively, in the serum of an individual. By way of example, here EP 0 648 228 B1, WO 03/87819 and FR 2 843 396 should be mentioned.

In US 2004/0018577, an immunoassay is disclosed which comprises at least three antibodies which all are capable of binding to different epitopes of an analyte. The analytes to be detected particularly concern the detection of markers regarding heart diseases, wherein i.a. also BNP and proBNP can be detected.

Biondo A. W. et al. (Vet. Pathol. 2003, 40(5):501-506) describe a method of detecting ANP and BNP in cats by means of polyclonal antibodies which are directed against a peptide of the ANP which comprises the amino acids 1 to 28, and against a peptide which comprises the amino acids 43 to 56 of proBNP, respectively.

In EP 1 016 867 A1, an immunoassay is described for the detection of preproBNP in mammals. There, antibodies are used which are directed against peptides comprising the amino acids 27 to 102, 73 to 102 and 27 to 64 of human BNP.

Jortani S. A. et al. (Clin. Chem. 2003, 50(2):265-278) describe the use of BNP and its prepro- and pro-forms as possible markers for heart diseases. In this article, no preferred peptide regions of BNP are mentioned which would be suitable for detecting heart diseases in dogs and cats.

In WO 2000/35951 several peptides are disclosed against which antibodies can be prepared, which are suitable in a method for diagnosing heart diseases. Three peptides comprising the amino acids 1 to 13, 37 to 49, and 65 to 76 of human Nt-pro-BNP protein are disclosed there, which may also be used for preparing antibodies that are directed against these peptides.

Moreover, several test kits for detecting human proBNP or the fragments thereof, respectively, are commercially available (e.g. from Roche and Biomedica). Nevertheless, there is no known method with whose assistance specifically proBNP in animal samples can be determined. Therefore, and because of the costly and complicated physical examinations of animals it is an object of the present invention to provide suitable means for determining proBNP or the fragments thereof, respectively.

SUMMARY OF THE INVENTION

Therefore, the present invention provides a method of determining feline or canine proBNP or fragments thereof, comprising the steps of providing a feline or canine sample, contacting the sample with at least one antibody which, when determining feline proBNP, or fragments thereof, binds to at least one epitope in the region comprising the amino acids 20 to 42 and/or in the region comprising the amino acids 57 to 80 of feline proBNP, and when determining canine proBNP, or fragments thereof, binds to at least one epitope in the region comprising the amino acids 20 to 86 of canine proBNP, and determining the presence and/or concentration of the feline or canine proBNP, or fragments thereof, present in the sample.

It has been found that an antibody which can bind to an epitope in the disclosed regions of the feline, or canine, proBNP, respectively, is very well suited to specifically determine proBNP.

It is pointed out that the feline and canine proBNP sequences herein disclosed have been used by way of example for the family of the felidae, or canidae, respectively, and that therefore individual amino acids which differ from the sequences disclosed herein, in the proBNP sequences of animals of other species of these families also fall within the scope of the sequences disclosed herein as long as these differing amino acids do not relate to the epitopes of the antibodies disclosed herein in a manner that a specific binding is no longer rendered possible. The amino acid sequences disclosed herein have been published in public data bases (e.g. Swiss-Prot: canine BNP—P16859 and feline BNP—Q9GLK4).

The samples used in the method according to the invention comprise fluid samples, such as, e.g., blood, urine, as well as tissue samples, such as, e.g., tissue sections of the cardiac muscle or of the brain. As required, the samples may be processed accordingly, so as to facilitate or render possible e.g. the later contacting of the sample with the antibodies according to the invention. Thus, fractions containing proBNP or fragments thereof, respectively, can be provided from blood samples, or also tissue samples may, e.g., be homogenized and likewise be separated from non-proteinaceous fractions.

The binding of at least one antibody to an epitope of the feline or canine proBNP in the sample means that the antibody is capable of binding an epitope in a defined sequence region of a specific protein, the at least one antibody not being capable of specifically binding epitopes of the protein outside of the defined region.

According to the invention, an antibody which is capable of binding an epitope may be used to determine proBNP or fragments thereof. Nevertheless, it may be advantageous to use several (e.g. two, three, four or five) antibodies which are capable of binding different epitopes of the proBNP.

The determination of the presence, or concentration, respectively, of the feline or canine proBNP, or fragment thereof, present in the sample can be effected by methods known in the prior art. By way of example, the carrying out of enzyme immunoassays (e.g. ELISA) may be mentioned in case of liquid samples or immunohistochemical methods in case of tissue samples.

"Antibodies" according to the present invention also comprise fragments of antibodies which are capable of recognizing an epitope according to the invention. Thus, an antibody may, e.g., merely consist of the F(ab) portion which exhibits the antigen-binding side. These antibody fragments may furthermore be part of a bispecific antibody or of a heterominibody (cf., e.g., EP 1 100 830 B1).

"proBNP or their fragments" according to the invention comprise all the proBNP fragments which are formed in vivo (e.g. Nt-proBNP) or in vitro (e.g. by mixing a sample with protease or with chemical substances, such as CNBr), and which have the epitopes according to the invention.

According to a preferred embodiment, the at least one antibody binds to at least one epitope in the region comprising the amino acids 25-35 and/or in the region comprising the amino acids 45-55 and/or in the region comprising the amino acids 60-80 of the feline proBNP.

It has been shown that primarily the above-indicated amino acid regions of the feline proBNP have epitopes which allow for a specific binding of antibodies.

In a method according to the present invention, several antibodies can be used which are capable of specifically binding several different epitopes on feline, or canine, respectively, proBNP. For this reason, at least one antibody which is capable of binding to at least one epitope can be used according to the invention. Furthermore, it should be mentioned that the amino acid regions indicated here may comprise not only one epitope, but, depending on their size, may comprise several epitopes. Thus, the method according to the invention comprises the use of a combination of several antibodies which are capable of specifically binding to at least one epitope.

According to the invention, when determining canine proBNP or fragments thereof, the at least one antibody binds to at least one epitope in the region comprising the amino acids 25-41 and/or in the region comprising the amino acids 55-65 and/or in the region comprising the amino acids 74-86 of the canine proBNP.

Antibodies which recognize epitopes in these regions are particularly well suited for determining proBNP or the fragments thereof in a sample of canine origin.

According to a preferred embodiment, the at least one epitope comprises at least three, at least four, at least five, at least six, at least seven, at least eight, at least nine, at least ten amino acids.

According to a preferred embodiment, the at least one antibody is polyclonal and/or monoclonal.

The antibodies employed in a method according to the invention may be polyclonal as well as monoclonal. For preparing these antibodies, peptide fragments comprising the amino acid regions disclosed herein of the feline and/or of the canine proBNP are used. These peptide fragments may be produced either synthetically, (Merrifield R. P., 1963, J Am Chem Soc 85, 2000, 149), recombinantly, or by chemical or enzymatic degradation of proBNP of recombinant or native origin. Depending on their size, the peptides recovered therefrom will be bound to an immunogenic carrier (e.g. KLH) or directly be used for preparing polyclonal or monoclonal antibodies (e.g. Köhler G. and Milstein C., 1975, Nature 256:495; Galfre et al., 1977, Nature 266:550). According to the invention, the antibodies may also be recombinantly prepared. Method for preparing recombinant antibodies are sufficiently known to the person skilled in the art (cf., e.g., Sambrook et al., Molecular Cloning, A Laboratory Manual, Cold Spring Harbor, Laboratory Press, 2001).

According to a further preferred embodiment, at least one further antibody binds to the at least one antibody or to the at least one epitope, whereby, for instance, it is rendered possible to carry out the inventive test as a sandwich assay.

The binding of a further antibody to the at least one antibody makes it possible to determine the latter and indirectly, the epitope bound to the at least one antibody qualitatively and quantitatively, respectively. If the at least one further antibody binds to the at least one epitope, it is possible to determine the binding of the at least one antibody to the at least one epitope qualitatively and quantitatively, respectively, via an enzyme immuno assay, e.g. if the at least one antibody is immobilized on a solid phase.

Preferably, the at least one antibody and/or the at least one further antibody is labelled.

In doing so, the at least one antibody and/or the at least one further antibody is labelled with an enzyme, such as peroxidase, in particular horseradish peroxidase, biotin, fluorescent dye, in particular fluorescein (FITC, DFTF), R-phycoerythrin (PE), peridinium chlorophyll protein (PerCP) and tandem conjugates, such as PE-Cy5 or PE-Texas Red, gold colloid or radionuclides.

By labelling one of the two antibodies, it is possible to determine in a secondary reaction, or also directly, the presence and/or the concentration of the labelled antibody bound to the at least one epitope. The antibodies themselves again can be detected by protein A conjugates (e.g., protein A gold conjugate).

According to a preferred embodiment, the at least one antibody or the at least one further antibody is bound to a solid phase.

By the binding of the at least one antibody or of the at least one further antibody, it is possible to produce, e.g., antibody chips, coated microtiter plates or lateral flow devices which can be used in a great number of methods.

Preferably, the determination of feline or canine proBNP or of fragments thereof is effected by a method selected from the group consisting of radioimmunoassay, immune binding assay, Western blot, immunohistochemistry, enzyme immunoassay, lateral flow device (LFD, test strips), and combinations thereof.

The above-mentioned methods are sufficiently known to the person skilled in the art. A survey of these methods is given e.g. in "Bioanalytik" (Lottspeich and Zorbas, Spektrum Verlag 1998). Lateral flow devices (LFD, test strips) are disclosed, e.g., in WO 02/059567.

According to a further aspect, the present invention relates to antibodies or antibody mixtures binding to at least one epitope in the region comprising the amino acids 20-42 and/or in the region comprising the amino acids 57-80 of feline proBNP.

According to a further preferred embodiment, the antibodies or the antibody mixtures bind to at least one epitope in the region comprising the amino acids 25-35 and/or in the region comprising the amino acids 45-55 and/or in the region comprising the amino acids 60-80 of the feline proBNP.

According to a further aspect, the present invention relates to an antibody or to an antibody mixture which binds to at least one epitope in the region comprising the amino acids 20-86 of the canine proBNP.

Preferably, the antibody or the antibody mixture binds to at least one epitope in the region comprising the amino acids 25-41 and/or in the region comprising the amino acids 55-65 and/or in the region comprising the amino acids 74-86 of the canine proBNP.

According to a preferred embodiment, the antibody or the antibody mixture binds to an epitope which comprises at least three, at least four, at least five, at least six, at least seven, at least eight, at least nine, at least ten amino acids. The epitopes according to the invention preferably have a length of 40 amino acids at the most, 35 amino acids at the most, 30 amino acids at the most, in particular 25 amino acids at the most, 20 amino acids at the most, or 15 amino acids at the most.

A further aspect of the present invention relates to a peptide comprising three amino acids in the region of the amino acids 20-42 and/or in the region comprising the amino acids 57-80 of the feline proBNP.

According to a further embodiment, the peptide comprises at least three amino acids in the region of the amino acids 25-35 and/or in the region of the amino acids 45-55 and/or in the region of the amino acids 60-80 of the feline proBNP.

A further aspect of the present invention relates to a peptide comprising three amino acids in the region of the amino acids 20-86 of the canine proBNP.

Preferably, the peptide comprises at least three amino acids in the region of the amino acids 25-41 and/or in the region comprising the amino acids 55-65 and/or in the region of the amino acids 74-86 of the canine proBNP.

According to a preferred embodiment, the peptide is chemically synthesized or isolated from a sample, or prepared recombinantly, respectively.

In order to appropriately prepare the epitope from a peptide which has been isolated from a sample or has been recombinantly produced, respectively, the latter may be further processed by enzymatic or chemical methods known per se.

A further aspect of the present invention relates to the use of an inventive antibody or of an antibody mixture for determining feline or canine proBNP or fragments thereof in the method according to the invention.

The peptides according to the invention can be used in competitive immunoassays in labelled form.

Preferably, the peptides according to the present invention are used for preparing an antibody or an antibody mixture.

Furthermore, the peptides according to the present invention are used as positive control or as a standard, respectively, for concentration determinations in a method according to the invention.

A further aspect of the present invention relates to a kit for determining feline or canine proBNP or fragments thereof, comprising at least one antibody according to the invention or at least one antibody mixture according to the invention, means for the qualitative and/or quantitative detection of a binding of the at least one antibody or of the at least one antibody mixture to feline or canine proBNP or fragments thereof, and, optionally, peptides according to the invention and/or feline or canine proBNP or fragments thereof as a positive control or as a standard for a concentration determination.

According to the invention, the kit may comprise at least one further antibody.

This additional antibody has an avidity to at least one antibody, or also to the at least one epitope.

According to a preferred embodiment, the at least one antibody and/or the at least one further antibody is labelled.

Preferably, the labelling comprises enzymes, such as peroxidases, in particular horseradish peroxidase, biotin, fluorescent dye, in particular fluorescein (FITC, DFTF), R-phycoerythrin (PE), peridinium chlorophyll protein (PerCP) and tandem conjugates, such as PE-Cy5 or PE-Texas Red, gold colloid or radionuclides.

A further aspect of the present invention relates to the use of a kit according to the invention in a method of determining feline or canine proBNP.

With the method of the present invention, it is possible not only to detect proBNP and its fragments in cats and dogs, but also in other mammals, such as horses, cattle, elephants, mice (Swiss-Prot: P40753), pigs (Swiss-Prot: P07634), rats (Swiss-Prot: P13205), camels (Swiss-Prot: Q6L7Z3) and sheep (Swiss-Prot: O46541) and fish, such as perch (Swiss-Prot: Q805E8), sturgeon (Swiss-Prot: P83965) and pufferfish (Swiss-Prot: Q805D7).

In order to detect proBNP in the above-mentioned animals, antibodies which bind to at least one epitope in an amino acid region of amino acid residue 1 to amino acid residue 80 of the corresponding proBNP are preferred. In particular antibodies are preferred which bind to at least one epitope comprising the amino acid regions 1-15, 15-30, 20-30, 25-35, 30-40, 35-50, 35-55, 45-55, 50-70, 60-70, 60-80 and 70-80. The following particularly preferred specific epitopes have also been found with the scheme lying at the basis of the present invention (cf. Examples).

TABLE 1

|  | Swiss-Prot No. | AA-Region |
| --- | --- | --- |
| Mouse | P40753 | 1-15, 20-30, 50-70 |
| Pig | P07634 | 20-30, 35-50, 60-70 |
| Rat | P13205 | 1-15, 30-40, 45-55, 60-80 |
| Camel | Q6L7Z3 | 20-30, 55-65, 70-80 |
| Sheep | O46541 | 1-15, 20-30, 45-55, 60-80 |
| Perch | Q805E8 | 15-30, 35-50, 70-80 |
| Sturgeon | P83965 | 1-20, 25-35, 70-80 |
| Pufferfish | Q805D7 | 15-30, 35-55, 60-80 |

As listed above for dogs and cats, the preferred lengths of the epitopes are also given for the above-mentioned animals.

The present invention is further illustrated by the following Examples and Figures without, however, being restricted thereto.

BRIEF DESCRIPTION OF THE DRAWINGS

FIG. 1 shows epitope recognition factors corresponding to the program ProtScale of the canine proBNP amino acid sequence (FIG. 1A) and amino acid sequences of the inventive canine proBNP epitope (FIG. 1B) (SEQ ID NOs: 1-5).

FIG. 2 shows epitope recognition factors of the feline proBNP amino acid sequence, calculated with ProtScale (FIG. 2A) and amino acid sequences of the inventive feline proBNP epitopes (FIG. 2B) (SEQ ID NOs: 6-9).

FIG. 3 shows standard curves based on ELISA assays using inventive antibodies with canine (FIG. 3A) and feline (FIG. 3B) proBNP. It could impressively be demonstrated that the proBNP determination with the inventive antibodies is linear over a wide concentration range.

DETAILED DESCRIPTION OF THE ILLUSTRATIVE EMBODIMENTS

Examples

Example 1

Preparing the Antibodies

Epitopes may, e.g. be determined by calculation with ProtScale (http://www.expasy.org/tools/protscale.html) according to the algorithm of Fraga S. ("Theoretical prediction of protein antigenic determinants from amino acid sequences.", 1982; Can. J. Chem. 60:2606-2610).

The peptide fragments were chosen from those regions of the amino acid sequence of the feline or canine Nt-proBNP, in which a maximum of the epitope recognition factors (corresponding to the results of the ProtScale program) was obtained, since these epitopes proved to be particularly immunogenic and readily accessible for antibodies. The selected peptides of the feline or canine proBNP were chemically synthesised and conjugated to a suitable carrier protein (KLH, e.g.).

One peptide/epitope each, conjugated to KLH, was injected into three sheep. For the first immunisation, each sheep received 0.5 mg of the corresponding antigen, mixed with Freund's Adjuvant (Guildhay, UK) and BCG (Bacillus Calmette-Guérin) and 0.25 mg of the immunogens to further increase the immune response.

According to the invention, it has been shown that the use of polyclonal antibodies yields very good and reproducible results. Nevertheless, the use of monoclonal antibodies in a method such as described in the present invention is also possible. Monoclonal antibodies against peptides/epitopes of the feline or canine proBNP can be prepared by standard methods known to the person skilled in the art (cf. in this respect e.g. Köhler G and Milstein C, Nature, 1975, 256:495-497).

Example 2

Determining the Antibody Reactivity by Means of ELISA

The reactivity of antibodies or sera, respectively, against peptides/epitopes of the proBNP which are recovered from the blood of the sheep was assayed by means of an ELISA test. At first, the microtiter plates were coated over night at 40° C. With Streptavidin (0.5 µg/ml, 200 µl per Well), washed, blocked With 1% BSA in 0.1 M PBS, pH 7.5, containing 0.25% of the detergent from SIGMA-ALDRICH® commercially available under the trademark TWEEN® 20, washed once more and incubated for 3 h at 40° C. With synthetic proBNP peptide sequences conjugated to biotin (0.25 µg/ml, 200 µl per Well). After a further washing step, the serum samples were diluted 1:1000/1:10000/1:100000 with 0.1 M phosphate buffer containing 3% BSA and applied to the microtiter plate. The binding of the antibodies to the peptides/epitopes on the plate was determined by the addition of anti-sheep-IgG antibodies which are conjugated with horseradish peroxidase, and of a substrate solution comprising TMB (tetramethyl-benzidine). The reaction of the horseradish peroxidase with TMB was stopped by adding 0.9% sulfuric acid. The colour development Was monitored With a photometer capable of analyzing microtiter plates.

Example 3

Nt-proBNP Measurement in Samples of Healthy and Sick Animals

Into the wells of a microtiter plate coated with one of the inventive antibodies, 20 µl of feline or canine serum were pipetted and incubated for 4-16 h at room temperature with 200 µl of a second, further peroxidase-labelled inventive antibody in 0.1 M phosphate buffer, pH 7. Subsequently, the microtiter plate was washed with 5×300 µl of 0.1 M phosphate buffer, pH 7, with 0.1% triton x 100, and 200 µl of tetramethyl benzidine were added as substrate. After a colour development of 20-30 minutes, the reaction is stopped by adding 50 µl of 0.9% sulfuric acid, and the colour intensity which is directly proportional to the amount of Nt-proBNP is measured with a microtiter plate photometer. The exact concentration is determined by a comparison with a calibration curve from recombinant feline or canine Nt-proBNP.

By way of example, in 8 healthy dogs and in 15 dogs suffering from heart disease the concentration of Nt-pro-BNP was determined by means of antibodies against the epitopes in the region of the amino acids 25-41 and 74-86 of the canine Nt-proBNP (Table 2):

TABLE 2

| State of Health | No. | Canine Nt-proBNP pmol/l |
|---|---|---|
| healthy | 1 | 862 |
|  | 2 | 1060 |
|  | 3 | 753 |
|  | 4 | 531 |
|  | 5 | 980 |
|  | 6 | 674 |
|  | 7 | 695 |
|  | 8 | 1010 |
| suffering from heart disease | 43 | 2460 |
|  | 44 | 1950 |
|  | 45 | 2140 |
|  | 46 | 2170 |
|  | 47 | 1480 |
|  | 48 | 1560 |
|  | 49 | 1390 |
|  | 50 | 1450 |
|  | 51 | 1520 |
|  | 52 | 1790 |
|  | 53 | 1310 |
|  | 54 | 1140 |
|  | 55 | 1975 |
|  | 57 | 1720 |
|  | 58 | 3020 |

These results show that with the antibodies of the present invention, the concentration of Nt-proBNP can efficiently be determined in the serum of animals, and with the results therefrom, a diagnosis on the state of health can be established, or the course of a therapy can be monitored, respectively.

Figure 1A:
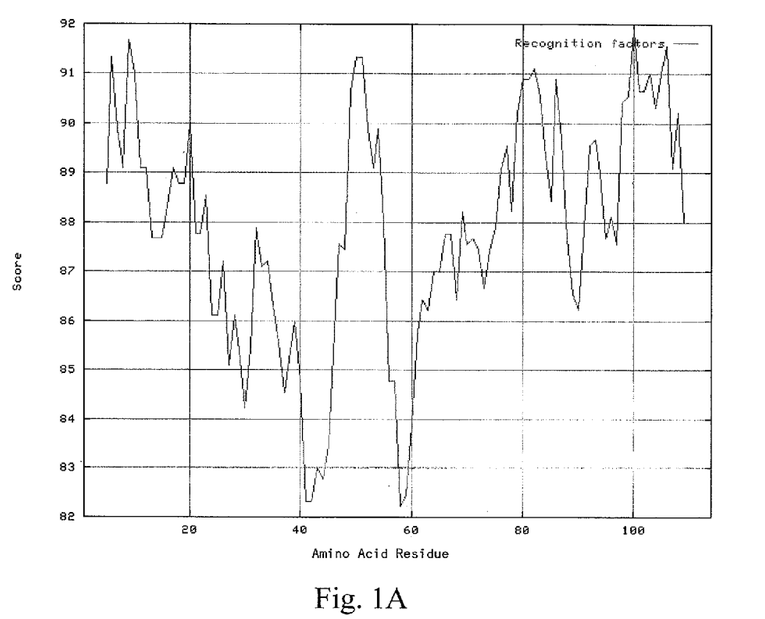
Figure 1B:
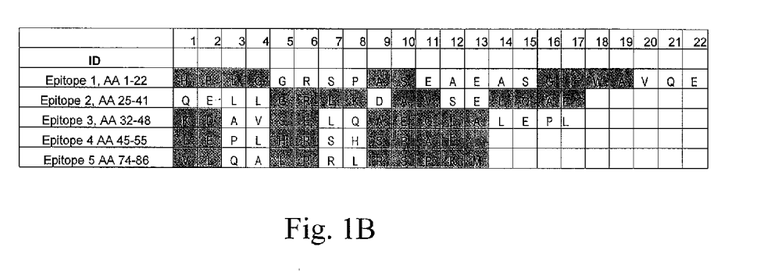
Figure 2A:
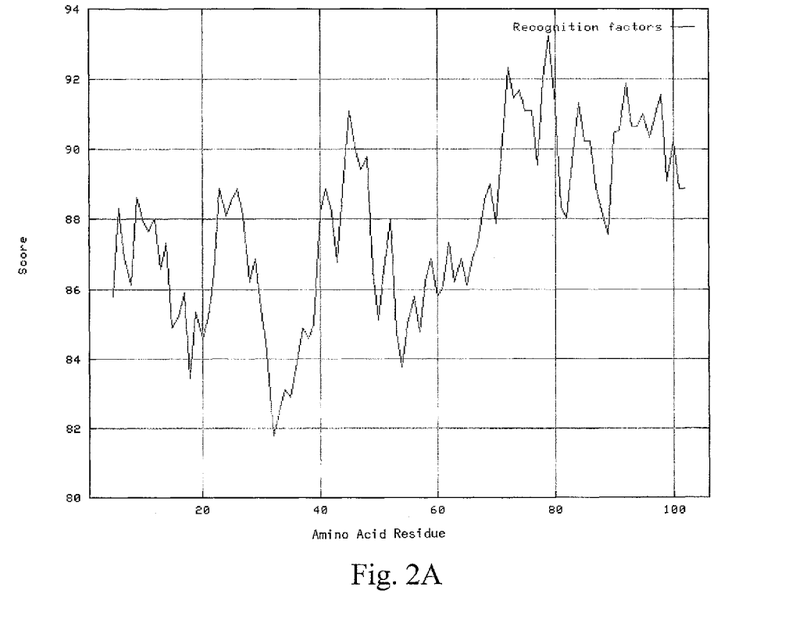
Figure 2B:
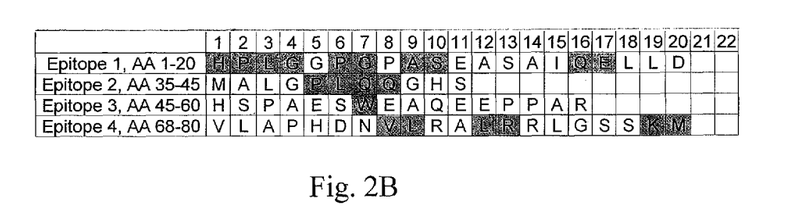
Figure 3A:
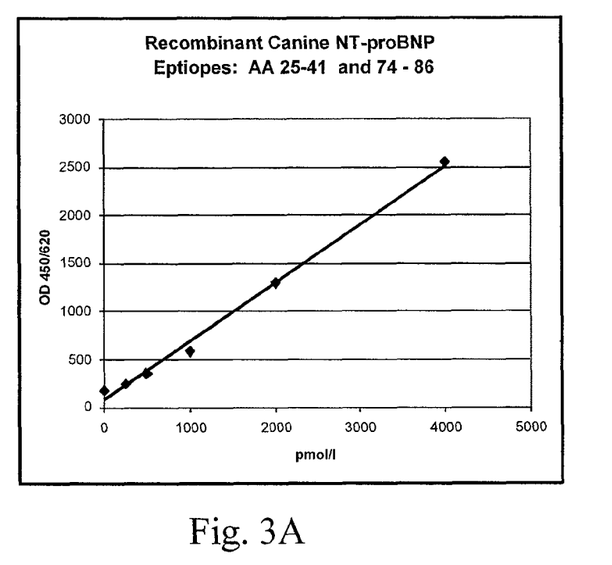
Figure 3B:
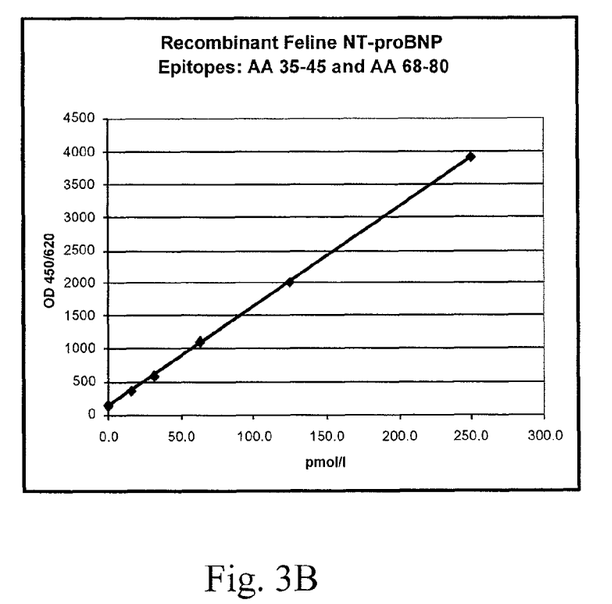
Figure 4:
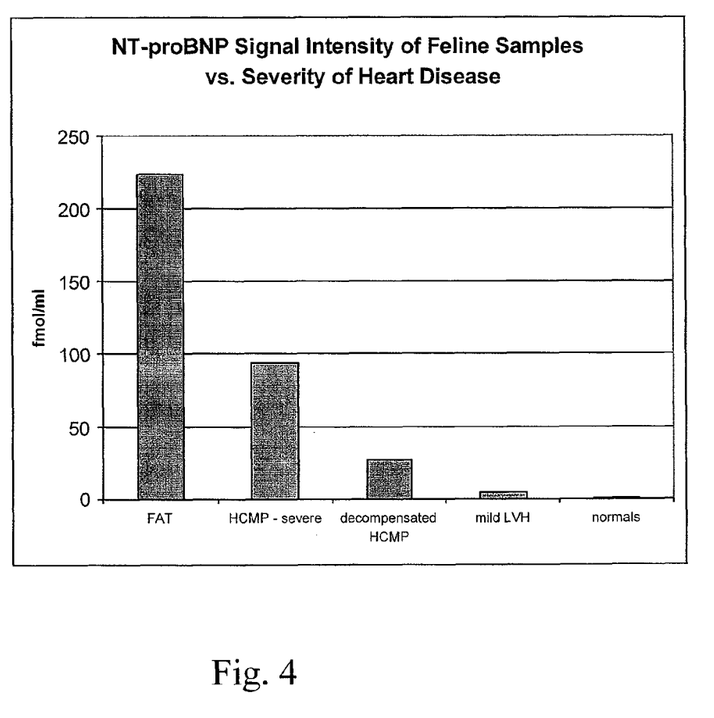
FIG. 4 shows the determination of proBNP in 47 sick and 28 healthy cats. The concentration of proBNP in the samples allows for determining the severity of the disease. FAT—feline atriale thrombosis, HCMP—hypertrophic cardiomyopathy, LVH—left ventricular hypertrophy.

Furthermore, FIG. 4 shows the determination of Nt-proBNP in 47 sick and 28 healthy cats. It was found that the concentration of detected Nt-proBNP directly correlates with the severity of the heart disease. In these tests, antibodies, which bind epitopes in the region comprising the amino acids 35 to 45 and 68 to 80 were used. The results obtained confirm numerous publications in which a similar connection had been postulated.

Example 4

Cross Reactivity

Recombinant feline, canine and human Nt-proBNP were coated on microtiter plates (250 ng/ml, 200 µl/well, over night, room temperature). Subsequently, the plates were washed and contacted with a dilution of the anti-human, anti-feline and anti-canine antisera (10-100 µg/ml, in 0.1 M phosphate buffer, pH 7). After a washing step, the amount of bound antibodies was measured with a suitable secondary antibody (peroxidase-labelled anti-sheep antibody). It has been shown that the respective antibodies react very well with the corresponding Nt-proBNP molecules (i.e., anti-feline antiserum with feline Nt-proBNP), but surprisingly do not react or react to a very slight extent with the Nt-proBNP molecules of the respective other species.

It could be demonstrated that the antibodies which were produced against the epitopes of the feline Nt-proBNP exhibit a high specificity and can bind to the corresponding human sequence to a very slight extent only. Since in the measurement of the antibody specificity Nt-proBNP was used as entire polypeptide as the binding partner and not the peptides which were used for producing the antibodies, it could impressively be demonstrated that the antibodies to feline epitopes of the Nt-proBNP do not exhibit any cross-reaction over the entire sequence region of the human Nt-proBNP. An exception is only that antibody which binds in the region of the amino acids 1 to 20 of feline Nt-proBNP. When binding to feline Nt-proBNP, this antibody shows only twice as high a relative reactivity than when binding to human Nt-proBNP.

Moreover, it could be demonstrated that antibodies against human epitopes of the Nt-proBNP also have a low reactivity relative to feline Nt-proBNP. Thus, it could be impressively be demonstrated that antibodies which are directed against epitopes of the human Nt-proBNP, cannot bind to feline Nt-proBNP and, thus, cannot be employed for determining Nt-proBNP in cats (cf. Table 3).

TABLE 3

| Antiserum No. | Antibody Specificity | Relative Reactivity | Rel. Reactivity Relative to the Corresponding Human Sequences |
|---|---|---|---|
| S2189 | AA 1-20 feline | 2.3 | 1.2 |
| S2190 | AA 45-55 feline | 3.7 | 0.01 |
| S2191 | AA 25-35 feline | 1.0 | 0.2 |
| S2192 | AA 60-80 feline | 4.2 | 0.3 |
| S2072 | AA 8-29 human | 0.4 | — |
| S2104 | AA 32-57 human | 0.25 | — |
| S2102 | AA 60-80 human | 1.7 | — |

The cross-reactivity was also tested with antibodies against epitopes of the canine Nt-proBNP and with antibodies against epitopes of the human Nt-proBNP. Also with canine sequences, a result comparable to the tests with feline sequences could be achieved (cf. Table 4)

TABLE 4

| Antiserum No. | Antibody Specificity | Relative Reactivity | Rel. Reactivity Relative to the Corresponding Human Sequences |
|---|---|---|---|
| S2195 | AA 1-22 canine | 2.2 | 1.1 |
| S2196 | AA 25-41 canine | 6.3 | 0.2 |
| S2197 | AA 55-65 canine | 1.0 | 0.03 |
| S2198 | AA 74-86 canine | 1.9 | 0.6 |
| S2072 | AA 8-29 human | 0.1 | — |
| S2104 | AA 32-57 human | 0.3 | — |
| S2102 | AA 60-80 human | 1.5 | — |

The invention claimed is:

1. A method for detecting feline proBNP or fragments thereof, the method comprising:

obtaining a blood sample from a feline subject;

contacting said blood sample with a first antibody raised against peptide sequence VLAPHDNVLRALRRLGSSKM (SEQ ID: 9) and a second antibody raised against peptide sequence MALGPLQQGHS (SEQ ID: 7); and detecting binding of the first antibody and the second antibody, thereby detecting feline proBNP or fragments thereof in the blood sample.

2. The method of claim 1, wherein said step of detecting binding is performed by radioimmunoassay.

3. The method of claim 1, wherein said step of detecting binding is performed by enzyme immunoassay.

4. The method of claim 1, wherein said first antibody or said second antibody is bound to a solid phase.

* * * * *

SEQUENCE LISTING

<160> NUMBER OF SEQ ID NOS: 9

<210> SEQ ID NO 1
<211> LENGTH: 22
<212> TYPE: PRT
<213> ORGANISM: Artificial
<220> FEATURE:
<223> OTHER INFORMATION: Synthetic peptide

<400> SEQUENCE: 1

His Pro Leu Gly Gly Arg Ser Pro Ala Ser Glu Ala Glu Ala Ser Gly
1               5                   10                  15

Leu Trp Ala Val Gln Glu
            20

<210> SEQ ID NO 2
<211> LENGTH: 17
<212> TYPE: PRT
<213> ORGANISM: Artificial
<220> FEATURE:
<223> OTHER INFORMATION: Synthetic peptide

<400> SEQUENCE: 2

Gln Glu Leu Leu Gly Arg Leu Lys Asp Ala Val Ser Glu Leu Gln Ala
1               5                   10                  15

Glu

<210> SEQ ID NO 3
<211> LENGTH: 17
<212> TYPE: PRT
<213> ORGANISM: Artificial
<220> FEATURE:
<223> OTHER INFORMATION: Synthetic peptide

<400> SEQUENCE: 3

Lys Asp Ala Val Ser Glu Leu Gln Ala Glu Gln Leu Ala Leu Glu Pro
1               5                   10                  15

Leu

<210> SEQ ID NO 4
<211> LENGTH: 12
<212> TYPE: PRT
<213> ORGANISM: Artificial
<220> FEATURE:
<223> OTHER INFORMATION: Synthetic peptide

<400> SEQUENCE: 4

Leu Glu Pro Leu His Arg Ser His Ser Pro Ala Glu
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic peptide

<400> SEQUENCE: 5

Val Leu Gln Ala Leu Arg Arg Leu Arg Ser Pro Lys Met
1               5                   10

<210> SEQ ID NO 6
<211> LENGTH: 20
<212> TYPE: PRT
<213> ORGANISM: Artificial

-continued

```
<220> FEATURE:
<223> OTHER INFORMATION: Synthetic peptide

<400> SEQUENCE: 6

His Pro Leu Gly Gly Pro Gly Pro Ala Ser Glu Ala Ser Ala Ile Gln
1               5                   10                  15

Glu Leu Leu Asp
            20

<210> SEQ ID NO 7
<211> LENGTH: 11
<212> TYPE: PRT
<213> ORGANISM: Artificial
<220> FEATURE:
<223> OTHER INFORMATION: Synthetic peptide

<400> SEQUENCE: 7

Met Ala Leu Gly Pro Leu Gln Gln Gly His Ser
1               5                   10

<210> SEQ ID NO 8
<211> LENGTH: 16
<212> TYPE: PRT
<213> ORGANISM: Artificial
<220> FEATURE:
<223> OTHER INFORMATION: Synthetic peptide

<400> SEQUENCE: 8

His Ser Pro Ala Glu Ser Trp Glu Ala Gln Glu Glu Pro Pro Ala Arg
1               5                   10                  15

<210> SEQ ID NO 9
<211> LENGTH: 20
<212> TYPE: PRT
<213> ORGANISM: Artificial
<220> FEATURE:
<223> OTHER INFORMATION: Synthetic peptide

<400> SEQUENCE: 9

Val Leu Ala Pro His Asp Asn Val Leu Arg Ala Leu Arg Arg Leu Gly
1               5                   10                  15

Ser Ser Lys Met
            20
```